United States Patent [19]
Saddoo et al.

[11] Patent Number: 5,386,637
[45] Date of Patent: Feb. 7, 1995

[54] BLADE HOLDING DEVICE

[75] Inventors: Lawrence C. Saddoo, Cheadle Hulme; Robert M. Williams, Hazel Grove, both of England

[73] Assignee: Ciba-Geigy Corporation, Ardsley, N.Y.

[21] Appl. No.: 140,582

[22] Filed: Oct. 21, 1993

[30] Foreign Application Priority Data

Oct. 29, 1992 [GB] United Kingdom ............... 9222748

[51] Int. Cl.⁶ .................................................. B26B 1/00
[52] U.S. Cl. .......................................... 30/338; 30/335
[58] Field of Search ............... 30/329, 332, 334, 335, 30/336, 337, 338, 506, 507

[56] References Cited

U.S. PATENT DOCUMENTS

| | | | |
|---|---|---|---|
| 1,492,553 | 5/1924 | Behrman | 30/335 |
| 2,172,680 | 9/1939 | Noreau, Jr. | 30/338 |
| 2,432,626 | 12/1947 | Lenk | 30/506 |
| 2,715,770 | 8/1955 | Meyer | 30/338 |

FOREIGN PATENT DOCUMENTS

| | | | |
|---|---|---|---|
| 88329 | 5/1922 | Germany | 30/338 |
| 625849 | 7/1949 | United Kingdom . | |
| 641307 | 8/1950 | United Kingdom . | |

Primary Examiner—Richard K. Seidel
Assistant Examiner—Hwei-Siu Payer
Attorney, Agent, or Firm—Irving M. Fishman; Karen C. Kaiser

[57] ABSTRACT

A blade holder for a manual cutting tool having a rigid open-ended frame shaped to provide support for a blade between the ends of the frame so that the cutting edge of the blade is proud of the ends of the frame, a clamp pivotally mounted on the frame, and a spring mounted on the frame and acting on the clamp. The clamp is moveable between an open position and a closed position. Manual pressure on the clamp against the spring forces the clamp apart from the ends of the frame to leave a gap (the open position) for the insertion or removal of a blade. Release of the manual pressure results in the spring holding the clamp against the ends of the frame (the closed position) so as to provide for retention of the blade in position between the clamp and the frame during a cutting operation.

17 Claims, 1 Drawing Sheet

BLADE HOLDING DEVICE

This invention relates to a blade holding device, particularly to a blade holding device for a manual cutting tool, especially one for use with very thin blades such as microtome blades.

Conventionally, microtome blades such as are used in histology when trimming necropsy tissue are held in handles similar to those of cutlery knives when effecting a cutting operation. However, the blades are very thin and tend to bend when cutting is carried out, making accurate cutting difficult. The device of the invention enables blades, particularly thin blades such as microtome blades, to be held in such a way that their tendency to bend is restricted and facilitates rapid mounting and replacement of blades.

Accordingly the present invention provides a blade holder for a manual cutting tool comprising a rigid open-ended frame shaped to provide means of supporting a blade between the ends of the frame so that a cutting edge of the blade is proud of the ends of the frame, a clamp pivotally mounted on the frame and spring means mounted on the frame and acting on the clamp, whereby the clamp is moveable between an open position wherein manual pressure on the clamp against the spring means forces the clamp apart from the ends of the frame to leave a gap for the insertion or removal of a blade and a closed position wherein on releasing the manual pressure the spring means holds the clamp against the ends of the frame, providing a means of retaining a blade in position between the clamp and the frame during a cutting operation.

In a blade holder of the invention, preferably each end of the frame is shaped to provide a surface against which the edge of a supported blade opposite the cutting edge abuts, thereby preventing movement of a supported blade in a direction opposite to the direction of a cutting force applied to the blade, and to provide a surface against which a face of a supported blade is held by the clamp.

In overall or general outline the frame may be C-shaped or, preferably, U-shaped comprising two sidearms linked by a crossarm, the term U-shaped being used in its general sense to cover shapes where the crossarm of the U is curved or straight (i.e. shapes which are curved or which have the configuration of three sides of a rectangle) and shapes where the crossarm is shorter or longer than, or the same length as, the sidearms. The ends of the frame may be bevelled, particularly where the frame is of metal, to avoid sharp edges.

In a convenient arrangement, the frame has a channel therein, the inner sidewall of the channel terminating short of the outer sidewall of the channel at each end of the frame to provide surfaces against which the edge of a supported blade opposite the cutting edge abuts and surfaces against which a face of a supported blade is held by the clamp. Preferably, the outer sidewall at each end of the frame provides a surface against which an end of a supported blade can abut.

Preferably, the clamp is a bar of similar shape to the frame. Thus, when the frame is U-shaped and has a channel as hereinbefore described, the clamp is preferably a U-shaped bar which is mounted pivotally on the frame by pins each passing through a sidearm of the bar and through the inner and outer sidewalls of a sidearm of the frame, and one or more springs acting on the crossarm of the bar are mounted in the crossarm of the frame, on the base of the channel in the frame, to hold the ends of the sidearms of the bar against the ends of the frame. Preferably there are two springs, especially coil springs, acting on the crossarm of the bar, one at substantially each end of the crossarm, these springs preferably being retained in recesses in the base of the channel in the frame. The centre of the crossarm of the bar conveniently bends away from the crossarm of the frame to facilitate the application of manual pressure on the bar against the spring(s).

The bar used as a clamp in the blade holder of the invention may be of generally rectangular or round, for example circular or oval, cross-section. Preferably it is of substantially circular cross-section along substantially all the length thereof. The ends of the bar may be bevelled, particularly where the bar is of metal, to avoid sharp edges.

A blade holder of the invention may have a handle attached to, or integral with the frame, to facilitate manual operation. Where the frame is U-shaped, the handle is conveniently attached to or, preferably, is integral with, a sidearm of the frame, extending outwardly therefrom in a direction transverse to the cutting direction of a supported blade. The handle may have a core attached to, or integral with, the frame and outer layers adhered or mechanically connected to the core to thicken the handle and thereby make it easier to grip.

The frame, the bar and, where present, the handle may each be of metal, lightweight metals such as aluminium being preferred, or a rigid plastics material.

The invention will now be further described, by way of example, with reference to the accompanying drawings, in which.

Figure 1:
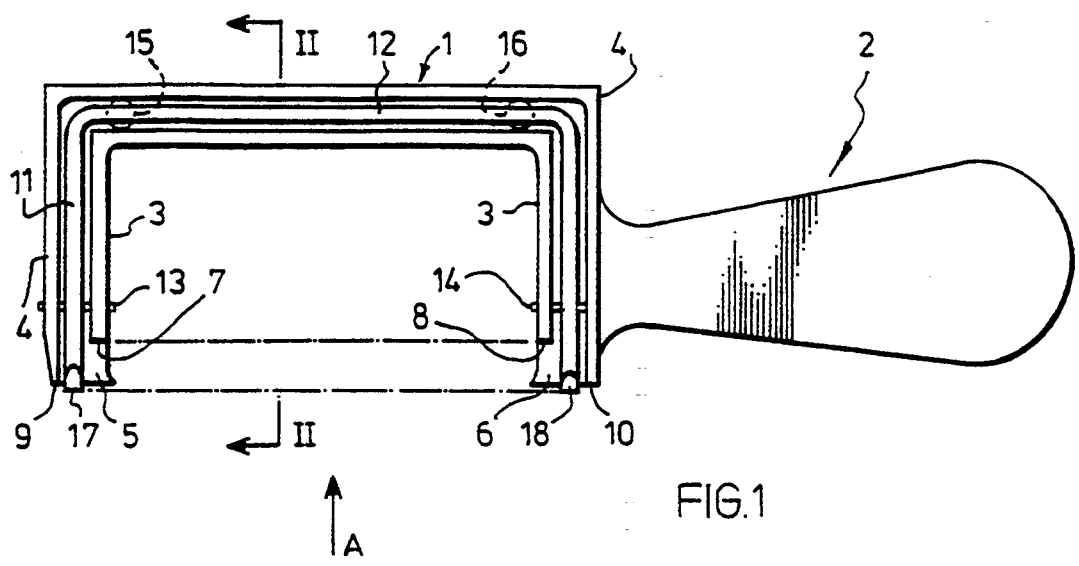
FIG. 1 is a plan view of a blade holder of the invention.
Figure 3:
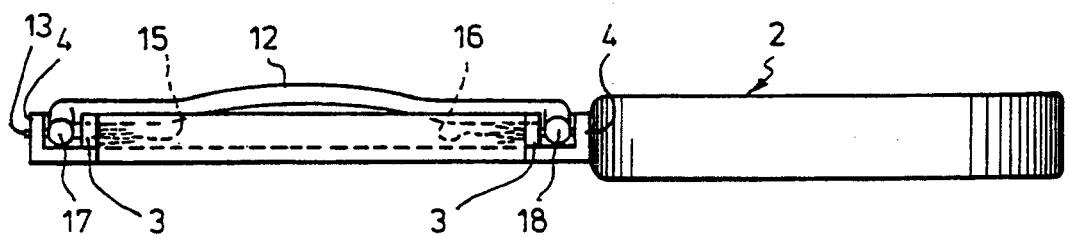
FIG. 3 is an end elevation from direction A in FIG. 1.
Figure 2:
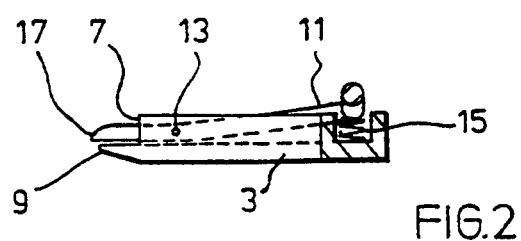
FIG. 2 is a cross-section along the line II—II in FIG. 1.

The blade holder consists of a rigid generally U-shaped frame 1 which is integral with a handle 2, the frame with integral handle being formed by machining of a single metal piece. The frame is formed with a channel, the inner sidewall 3 of the channel terminating short of the outer sidewall 4 at each end of the frame to provide surfaces 5 and 6 against which a face of a blade can be held and surfaces 7 and 8 against which the edge of a blade opposite the cutting edge can abut when a blade is supported in a cutting position with the cutting edge standing proud of the bevelled ends 9 and 10 of the frame.

A metal clamping bar 11, of similar shape to the frame, but bent away from the frame in the region 12, is pivotally mounted on the frame through metal pins 13 and 14 passing through the sidewalls of the frame. Springs 15 and 16 are located in recesses in the base of the channel in the crossarm of the frame to act on the clamping bar so that the bevelled ends 17 and 18 of the bar are held against the surfaces 5 and 6 and, when pressure is applied to the bar in the region 12 against the springs, the ends 17 and 18 of the bar are forced away from the surfaces 5 and 6 to create a gap into which a blade can be inserted between the ends of the bar and the surfaces 5 and 6, with the edge of the blade opposite its cutting edge abutting against the surfaces 7 and 8 of the frame and the ends of the blade abutting against the outer sidewall 4 of the frame. On release of the pressure applied to the bar, the springs 15 and 16 again act on the bar to hold the ends 17 and 18, and therefore a face of the inserted blade, against the surfaces 5 and 6. An inserted blade can thereby be supported and retained in position during a cutting operation, during which the blade holder is manipulated by the handle 2.

What is claimed is:

1. A blade holder for a manual cutting tool comprising a rigid open-ended frame shaped to provide means for supporting a blade between two opposite ends of the frame so that a cutting edge of the blade extends beyond the ends of the frame, a clamp pivotally mounted on the frame and spring means mounted on the frame and acting on the clamp, whereby the clamp is moveable between an open position wherein manual pressure on the clamp against the spring means forces the clamp apart from the ends of the frame to leave a gap for insertion or removal of the blade and a closed position wherein on releasing the manual pressure the spring means holds the clamp against the ends of the frame, thereby providing a means for retaining the blade in position between the clamp and the frame during a cutting operation, in which the frame has a channel which has inner and outer sidewalls, the inner sidewall of the channel terminating short of the outer sidewall of the channel at each end of the frame to provide surfaces against which an edge of the supported blade opposite the cutting edge abuts and surfaces against which a face of the supported blade is held by the clamp.

2. A blade holder according to claim 1, in which the frame is U-shaped, comprising two sidearms linked by a crossarm.

3. A blade holder according to claim 2, in which the clamp is a bar of similar shape to the frame.

4. A blade holder according to claim 1, in which the clamp is a bar of similar shape to the frame.

5. A blade holder according to claim 1, in which the frame is U-shaped, the clamp is a U-shaped bar having two sidearms linked by a crossarm, said bar being mounted pivotally on the frame by pins each passing through a respective sidearm of the bar and through inner and outer sidewalls of a sidearm of the frame, and at least one spring acting on the crossarm of the bar is mounted in a crossarm of the frame, on the base of the channel in the frame, to hold the ends of the sidearms of the bar against the ends of the frame.

6. A blade holder according to claim 5, in which there are two springs acting on the crossarm of the bar, respectively at substantially each end of the crossarm of the bar.

7. A blade holder according to claim 6, in which said springs are retained in recesses in the base of the channel in the frame.

8. A blade holder according to claim 6, in which the crossarm of the bar bends at the centre thereof away from the crossarm of the frame to facilitate application of manual pressure on the bar against the springs.

9. A blade holder according to claim 5, in which the crossarm of the bar bends at the centre thereof away from the crossarm of the frame to facilitate application of manual pressure on the bar against at least one spring.

10. A blade holder according to claim 5, in which the bar is of substantially circular cross-section along substantially the entire length thereof.

11. A blade holder according to claim 10, in which the ends of the sidearms of the bar are bevelled.

12. A blade holder according to claim 1 which has a handle attached thereto or integral therewith.

13. A blade holder according to claim 12 in which the frame is U-shaped and the handle is attached to, or in integral with, a sidearm of the frame, said handle extending outwardly therefrom in a direction transverse to a cutting direction of the supported blade.

14. A blade holder for a manual cutting tool comprising a rigid open-ended frame shaped to provide means for supporting a blade between two opposite ends of the frame so that a cutting edge of the blade extends beyond the ends of the frame, a clamp pivotally mounted on the frame and spring means mounted on the frame and acting on the clamp, whereby the clamp is moveable between an open position wherein manual pressure on the clamp against the spring means forces the clamp apart from the ends of the frame to leave a gap for insertion or removal of the blade and a closed position wherein on releasing the manual pressure the spring means holds the clamp against the ends of the frame, thereby providing a means for retaining the blade in position between the clamp and the frame during a cutting operation, each of said ends of said frame being shaped to provide a surface against which an edge of the supported blade opposite said cutting edge abuts, thereby preventing movement of the supported blade in a direction opposite to the direction of a cutting force applied to said blade, and to provide a surface against which a face of the supported blade is held by the clamp.

15. A blade holder according to claim 14, in which the frame is U-shaped, comprising two sidearms linked by a crossarm.

16. A blade holder according to claim 14, which has a handle attached thereto or integral therewith.

17. A blade holder according to claim 16, in which the frame is U-shaped and the handle is attached to, or is integral with, a sidearm of the frame, said handle extending outwardly therefrom in a direction transverse to a cutting direction of the supported blade.

* * * * *